US012115350B2

(12) United States Patent
Ogahara

(10) Patent No.: US 12,115,350 B2
(45) Date of Patent: Oct. 15, 2024

(54) MEDICAL APPARATUS

(71) Applicant: TERUMO KABUSHIKI KAISHA, Tokyo (JP)

(72) Inventor: Atsushi Ogahara, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 904 days.

(21) Appl. No.: 17/187,047

(22) Filed: Feb. 26, 2021

(65) Prior Publication Data

US 2021/0178065 A1 Jun. 17, 2021

Related U.S. Application Data

(63) Continuation of application No. PCT/JP2019/021540, filed on May 30, 2019.

(30) Foreign Application Priority Data

Aug. 27, 2018 (JP) ................. 2018-158757

(51) Int. Cl.
*A61M 5/172* (2006.01)
*A61M 5/145* (2006.01)
*G06F 3/044* (2006.01)

(52) U.S. Cl.
CPC ............. *A61M 5/172* (2013.01); *G06F 3/044* (2013.01); *A61M 5/1452* (2013.01)

(58) Field of Classification Search
CPC ...... A61M 5/172; A61M 5/1452; G06F 3/044
See application file for complete search history.

(56) References Cited

U.S. PATENT DOCUMENTS

| 5,366,346 | A | * | 11/1994 | Danby | ................ | A61M 5/172 |
| | | | | | | 417/18 |
| 10,709,835 | B2 | * | 7/2020 | Clarke | ................ | G16H 20/17 |
| 2004/0178995 | A1 | | 9/2004 | Sterling | | |
| 2014/0046296 | A1 | * | 2/2014 | Clarke | ................ | A61M 5/1456 |
| | | | | | | 604/152 |

FOREIGN PATENT DOCUMENTS

| CN | 101061507 A | 10/2007 |
| CN | 102317892 A | 1/2012 |

(Continued)

OTHER PUBLICATIONS

Extended European Search Report, dated Jul. 6, 2021, issued in European Application No. 19854195.5, (7 pages).

(Continued)

*Primary Examiner* — Michael Pervan
(74) *Attorney, Agent, or Firm* — Foley & Lardner LLP

(57) ABSTRACT

A medical apparatus includes an operation reception unit, a position acquisition unit that can acquire position information of a detection target based on a position of the detection target on the operation reception unit at an acquisition time that occurs in a predetermined cycle, the detection target being in contact with or proximate to the operation reception unit, and a control unit that determines an operation position of the detection target on the operation reception unit at a last acquisition time before a latest acquisition time, on the basis of the position information acquired at the latest acquisition time.

13 Claims, 8 Drawing Sheets

(56) References Cited

FOREIGN PATENT DOCUMENTS

| | | | |
|---|---|---|---|
| CN | 102385459 A | 3/2012 | |
| CN | 104777995 A | 7/2015 | |
| CN | 111032121 A | 4/2020 | |
| EP | 0 916 353 A1 | 5/1999 | |
| JP | 2004-024884 A | 1/2004 | |
| JP | 2007-306990 A | 11/2007 | |
| JP | 2014-059633 A | 4/2014 | |
| JP | 2016-115042 A | 6/2016 | |
| JP | 2017-213057 A | 12/2017 | |
| WO | WO-2007072316 A2 * | 6/2007 | ........... G06F 3/0338 |
| WO | WO-2013/061607 A1 | 5/2013 | |

OTHER PUBLICATIONS

International Searching Authority, "Written Opinion," issued in connection with PCT Patent Application No. PCT/JP2019/021540, dated Jul. 16, 2019.
Chinese Office Action issued in connection with CN Appl. Ser. No. 201980008754.2, dated May 18, 2022.
International Searching Authority, "International Search Report," issued in connection with International Patent Application No. PCT/JP2019/021540, dated Jul. 16, 2019.
International Searching Authority, "Written Opinion," issued in connection with International Patent Application No. PCT/JP2019/021540, dated Jul. 16, 2019.

* cited by examiner

FIG. 5

|  | TWO ACQUISITION TIMING BEFORE | ONE ACQUISITION TIMING BEFORE | LATEST ACQUISITION TIMING |
|---|---|---|---|
| POSITION INFORMATION | AREA h | AREA a | AREA a |
| OPERATION POSITION | AREA g | AREA a | UNDETERMINED |

FIG. 6

|  | TWO ACQUISITION TIMING BEFORE | ONE ACQUISITION TIMING BEFORE | LATEST ACQUISITION TIMING |
|---|---|---|---|
| POSITION INFORMATION | AREA h | AREA a | AREA b |
| OPERATION POSITION | AREA g | AREA g | UNDETERMINED |

FIG. 7

|  | TWO ACQUISITION TIMING BEFORE | ONE ACQUISITION TIMING BEFORE | LATEST ACQUISITION TIMING |
|---|---|---|---|
| POSITION INFORMATION | AREA h | AREA a | AREA b |
| OPERATION POSITION | AREA g | AREA a | UNDETERMINED |

FIG. 8

|  | TWO ACQUISITION TIMING BEFORE | ONE ACQUISITION TIMING BEFORE | LATEST ACQUISITION TIMING |
|---|---|---|---|
| POSITION INFORMATION | AREA h | AREA a | NO TOUCH |
| OPERATION POSITION | AREA g | NO TOUCH | UNDETERMINED |

MEDICAL APPARATUS

CROSS-REFERENCE TO RELATED APPLICATIONS

This application is a bypass continuation of PCT Application No. PCT/JP2019/021540, filed on May 30, 2019, which claims priority to Japanese Application No. 2018-158757, filed on Aug. 27, 2018. The contents of these applications are hereby incorporated by reference in their entireties.

TECHNICAL FIELD

The present disclosure relates to a medical apparatus and, in particular, to a medical apparatus that receives input operation by an operator.

BACKGROUND

There is known a medical apparatus that includes an input device that receives input operation by an operator, sets a setting value on the basis of the received input operation, and operates on the basis of the set setting value. Examples of such a medical apparatus include a syringe pump in which a syringe containing liquid, such as liquid medicine, is placed, the syringe pump being configured to deliver the liquid into a living body of a patient, or the like, while controlling a flow rate by controlling pushing speed of a pusher of the placed syringe, according to a setting value set by an operator. In a medical apparatus such as a syringe pump, for example, a rotary member such as a dial may be used as an input device used to set a predetermined setting value for an administration rate, or the like, and the setting value can be increased or decreased according to a rotation amount of the rotary member (e.g., refer to JP 2004-24884 A).

SUMMARY

In a medical apparatus using a rotary member as an input device, a gap is likely to be formed between the rotary member and a member, such as a housing, provided with the rotary member. There has been a possibility that the rotary member is difficult to rotate, and that operability is reduced, by liquid such as highly viscous liquid medicine or another foreign substance entering into such a gap.

An object of the present disclosure is to provide a medical apparatus capable of limiting reduction in operability even if a foreign substance such as liquid adheres.

A medical apparatus as a first aspect of the present invention includes an operation reception unit, a position acquisition unit that can acquire position information of a detection target based on a position of the detection target on the operation reception unit at an acquisition time that occurs in a predetermined cycle, the detection target being in contact with or proximate to the operation reception unit, and a control unit that determines an operation position of the detection target on the operation reception unit at a last acquisition time before a latest acquisition time, on the basis of the position information acquired at the latest acquisition time.

In the medical apparatus as an embodiment of the present invention, the control unit determines, on the basis of position information acquired at the latest acquisition time and at a last acquisition time before the latest acquisition time, the operation position at the last acquisition time before.

In the medical apparatus as an embodiment of the present invention, in a case in which the position information is not acquired at at least one of the latest acquisition time or at the last acquisition time before, the control unit determines that the detection target is not in the operation position on the operation reception unit at the last acquisition time before.

In the medical apparatus as an embodiment of the present invention, in a case in which an operation mode is in a predetermined operation mode, and position information acquired at the latest acquisition time and position information acquired at the last acquisition time before match, the control unit determines a position indicated by the matched position information as the operation position.

In the medical apparatus as an embodiment of the present invention, in a case in which an operation mode is in a predetermined operation mode, and position information acquired at the latest acquisition time and position information acquired at the last acquisition time before do not match, the control unit determines an operation position at a second to last acquisition time before the latest acquisition time as the operation position.

In the medical apparatus as an embodiment of the present invention, the predetermined operation mode is a mode that detects low-speed input by the detection target.

In the medical apparatus as an embodiment of the present invention, in a case in which the detection target is moving in a state of being in contact with or proximate to the operation reception unit at a speed of a predetermined threshold or lower, the control unit operates in a mode that detects the low-speed input.

In the medical apparatus as an embodiment of the present invention, in a case in which an operation mode is not in the predetermined operation mode, the control unit determines a position indicated by position information acquired at a last acquisition time before the latest acquisition time as the operation position.

In the medical apparatus as an embodiment of the present invention, the control unit increases or decreases a predetermined setting value on the basis of a change in the determined operation position in a circumferential direction around a predetermined center point on the operation reception unit.

In the medical apparatus as an embodiment of the present invention, the position acquisition unit has a plurality of detection regions arranged along the circumferential direction, and acquires any one of the plurality of detection regions as the position information.

According to the medical apparatus of the present disclosure, it is possible to limit reduction in operability even if a foreign substance such as liquid adheres.

BRIEF DESCRIPTION OF THE DRAWINGS

FIG. 5 illustrates a diagram for describing an example of a method for determining an operation position by the syringe pump illustrated in FIG. 1.

FIG. 6 illustrates a diagram for describing an example of a method for determining an operation position by the syringe pump illustrated in FIG. 1.

FIG. 7 illustrates a diagram for describing an example of a method for determining an operation position by the syringe pump illustrated in FIG. 1.

FIG. 8 illustrates a diagram for describing an example of a method for determining an operation position by the syringe pump illustrated in FIG. 1.

DETAILED DESCRIPTION

Figure 1:
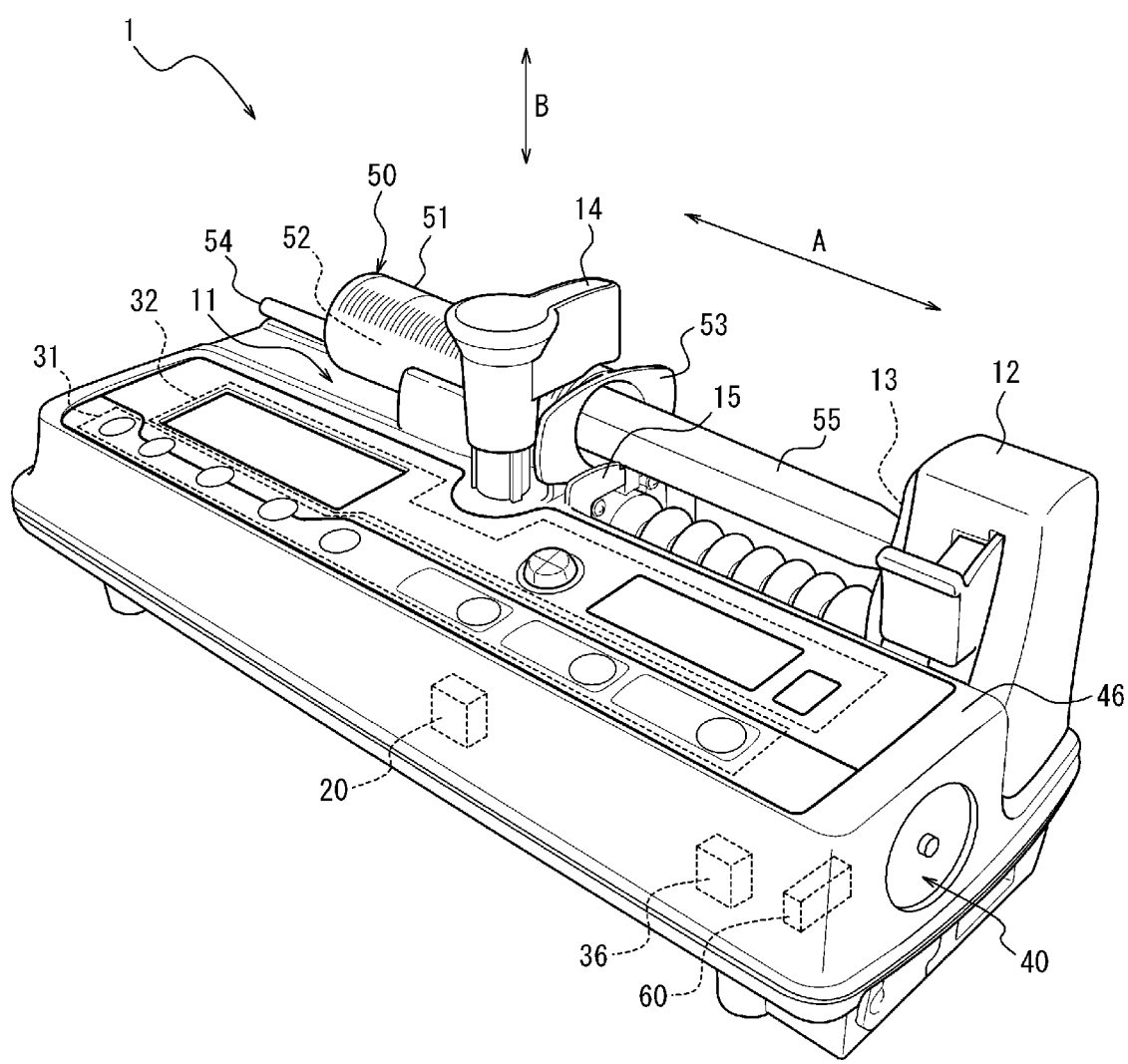
FIG. 1 illustrates a perspective view of a syringe pump as a medical apparatus according to an embodiment of the present invention.
Figure 2:
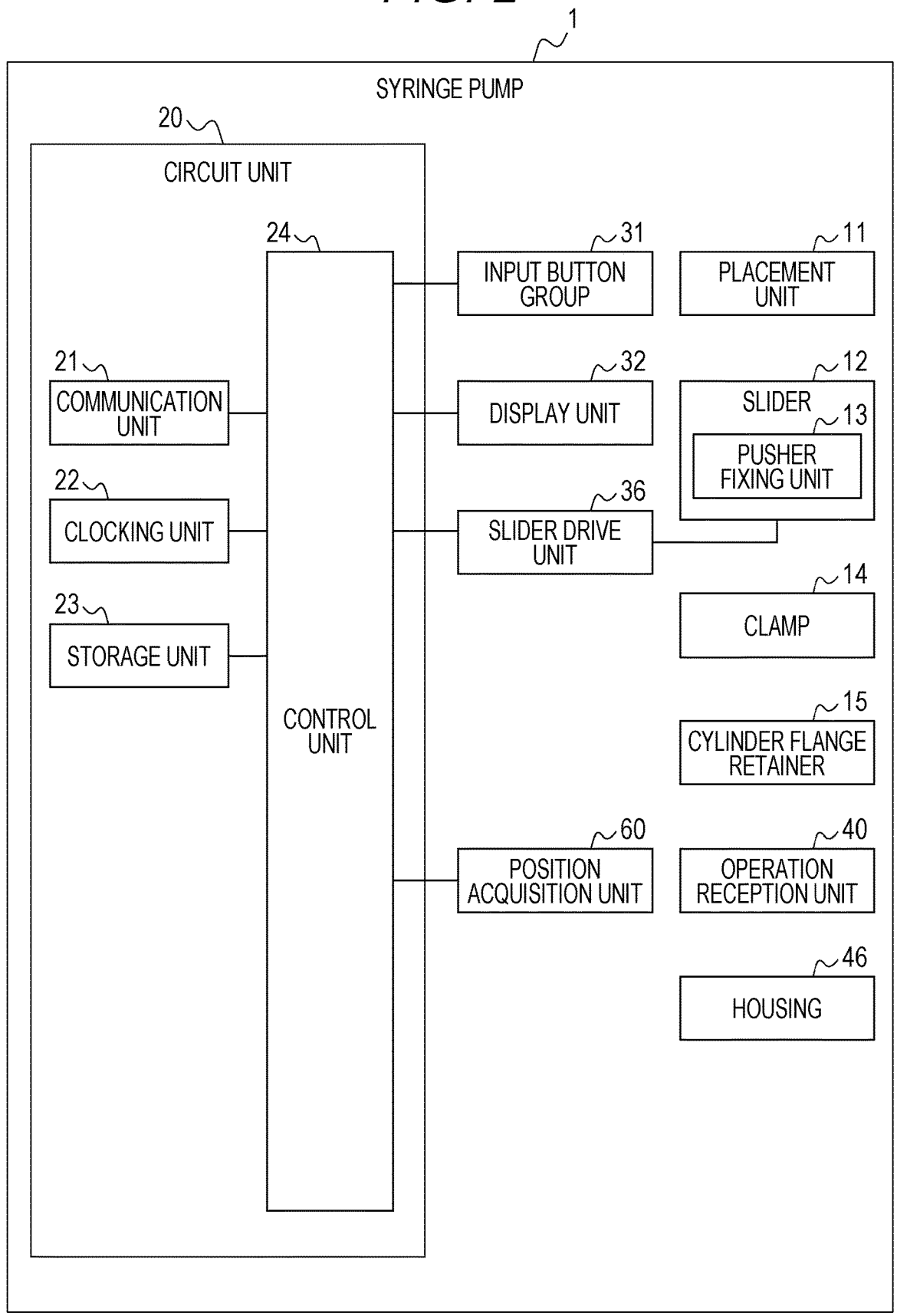
FIG. 2 illustrates a block diagram of a configuration of the syringe pump illustrated in FIG. 1.

An embodiment of the present invention will be described below with reference to the drawings. In each figure, common components are denoted by the same reference signs.
[Configuration of Syringe Pump]
FIG. 1 illustrates a perspective view of a syringe pump 1 as a medical apparatus according to an embodiment of the present invention. FIG. 1 illustrates the syringe pump 1 on which a syringe 50 is placed. As illustrated in FIG. 1, the syringe pump 1 is configured as a pump that delivers liquid contained in a hollow part 52 of the syringe 50. FIG. 2 illustrates a block diagram of a configuration of the syringe pump 1.

As illustrated in FIGS. 1 and 2, the syringe pump 1 includes a placement unit 11, a slider 12, a clamp 14, a cylinder flange retainer 15, a circuit unit 20, an input button group 31, a display unit 32, a slider drive unit 36, an operation reception unit 40, a housing 46, and a position acquisition unit 60.

As illustrated in FIG. 1, the syringe 50 can be placed on the placement unit 11. The syringe 50 placed on the placement unit 11 has a cylinder 51 that has a cylindrical shape and defines the hollow part 52 inside, and a pusher 55 that is inserted from a base end side of the cylinder 51 into the hollow part 52 and is movable, in the hollow part 52, along an extending direction A of the cylinder 51 (hereinafter simply described as "extending direction A"), while adhering without a gap to an inner circumferential surface of the cylinder 51 in a circumferential direction. The cylinder 51 has a cylinder flange 53 at a base end part, and defines, at a tip end part, an outlet hole 54 that communicates the hollow part 52 with an outside. A flexible tube can be connected to the tip end part of the cylinder 51. When the tube is connected to the tip end part of the cylinder 51, the outlet hole 54 communicates with a fluid path defined by the tube. Liquid such as liquid medicine is contained in the hollow part 52 of the syringe 50. Hereinafter, of the extending direction A, a tip end side of the cylinder 51 is described as a "tip end side of the extending direction A", and the base end side of the cylinder 51 is described as a "base end side of the extending direction A".

As illustrated in FIG. 1, the cylinder 51 of the syringe 50 can be placed on the placement unit 11. Furthermore, as illustrated in FIG. 1, when the cylinder 51 of the syringe 50 is placed on the placement unit 11, the cylinder flange retainer 15 stores a portion of the cylinder flange 53. With this arrangement, the position of the cylinder 51 with respect to the syringe pump 1 is fixed.

As illustrated in FIG. 1, the slider 12 has a pusher fixing unit 13. The slider 12 is movable so as to engage with the pusher 55 of the syringe 50 placed on the placement unit 11. Specifically, at a position to the base end side of the extending direction A from the pusher 55 of the syringe 50 placed on the placement unit 11, the slider 12 is movable along the extending direction A. With the pusher fixing unit 13, the slider 12 fixes the pusher 55 of the syringe 50 placed on the placement unit 11. In a state where the pusher 55 is fixed to the slider 12 by the pusher fixing unit 13, the pusher 55 moves integrally with the slider 12 as the slider 12 moves along the extending direction A. At this time, the cylinder 51 placed on the placement unit 11 is fixed to the syringe pump 1 by the cylinder flange retainer 15 in the extending direction A. Therefore, when the slider 12 moves to the tip end side of the syringe 50, the pusher 55 moves to the tip end side with respect to the cylinder 51, and the liquid contained in the hollow part 52 is discharged from the outlet hole 54. For this reason, the liquid contained in the hollow part 52 can be delivered toward a living body through the fluid path defined by the tube connectable to the tip end part of the cylinder 51.

As illustrated in FIG. 1, the clamp 14 is movable along a direction B orthogonal to the extending direction A and can fix the cylinder 51 of the placed syringe 50 so that the cylinder 51 is sandwiched between the clamp 14 and the placement unit 11. Furthermore, the cylinder 51 is fixed to the syringe pump 1 firmly, because fixing the cylinder 51 with the clamp 14 makes a portion of the cylinder flange 53 difficult to come off the cylinder flange retainer 15.

As illustrated in FIG. 2, the circuit unit 20 includes a communication unit 21, a clocking unit 22, a storage unit 23, and a control unit 24.

The communication unit 21 includes an interface that transmits or receives information to or from an external information processing device, such as a computer, by wireless communication or wire communication.

The clocking unit 22 measures time and keeps time. The clocking unit 22 may be implemented by, for example, a real time clock (RTC). The clocking unit 22 may be implemented as one function of the control unit 24.

The storage unit 23 is configured to include, for example, a storage device and stores various pieces of information and programs. Specifically, the storage unit 23 stores a program for performing setting value increase/decrease processing, various pieces of input support processing, or the like, which is performed by the control unit 24. Furthermore, the storage unit 23 stores information about a predetermined setting value for a flow rate, a dosage, or the like of liquid delivered by the syringe pump 1, a control program for delivering the liquid by driving the slider drive unit 36 on the basis of the predetermined setting value, or the like. Furthermore, the storage unit 23 stores the position information acquired by the position acquisition unit 60. Details of position information that the storage unit 23 stores will be described below.

The control unit 24 includes a processor that implements a predetermined function by reading a predetermined piece of information and program, for example, from among the various pieces of information and programs stored in the storage unit 23, and the control unit 24 controls overall operation of the syringe pump 1. As will be described below, the control unit 24 identifies operation input from the operation reception unit 40 by a detection target, such as a fingertip of an operator. Specifically, the control unit 24 reads the predetermined piece of information and program stored in the storage unit 23, and performs operation position determination processing, setting value increase/decrease processing, various pieces of input support processing, or the like. Details of the operation position determination processing and the setting value increase/decrease processing will be described below. The control unit 24 transmits or receives information to or from an external information processing device via the communication unit 21. The control unit 24 performs various pieces of processing on the basis of information input from the input button group 31 and the position acquisition unit 60, and outputs, from the display unit 32, information associated with the performing of the various pieces of processing.

As illustrated in FIG. 1, the input button group 31 is arranged on a surface of the housing 46 and includes various operation buttons configured to receive an input operation by the operator. The input button group 31 includes, for example, a power button for switching on and off operation power supply of the syringe pump 1, a start button for starting liquid delivery, and a stop button for stopping liquid delivery. The input button group 31 outputs input information to the control unit 24.

As illustrated in FIG. 1, the display unit 32 includes, for example, a display device such as a liquid crystal display, an organic EL display, or the like. On the basis of a signal from the control unit 24, the display unit 32 displays a setting value or measured value of a flow rate of liquid to be delivered, a setting value or measured value of a dosage of liquid to be delivered, various pieces of alarm information, or the like.

The slider drive unit 36 includes, for example, a motor, and moves the slider 12 along the extending direction A (refer to FIG. 1) on the basis of a signal from the control unit 24.

As illustrated in FIG. 1, the operation reception unit 40 is arranged so that at least a portion of the operation reception unit 40 is exposed to an outside of the syringe pump 1. Details of the operation reception unit 40 will be described below.

The position acquisition unit 60 can acquire position information based on a position, with respect to the operation reception unit 40, of the detection target, such as the fingertip of the operator, in contact with or proximate to the operation reception unit 40. The position acquisition unit 60 acquires position information at a predetermined acquisition time. The predetermined acquisition time occurs, for example, in a predetermined cycle. The predetermined acquisition time occurs, for example, every 10 milliseconds. In this case, the position acquisition unit 60 acquires position information every 10 milliseconds. However, the predetermined cycle is not limited to 10 milliseconds. The predetermined cycle may be determined as appropriate according to an application, a specification, or the like of the operation reception unit 40. The position acquisition unit 60 outputs the acquired position information to the control unit 24.

The position acquisition unit 60 is an electric field type position detection sensor that can acquire position information of the detection target by, for example, generating an electric field around the operation reception unit 40 and detecting disturbance of the electric field generated by the detection target coming proximate to the operation reception unit 40. Alternatively, the position acquisition unit 60 can be a capacitance type position detection sensor that can acquire position information of the detection target by, for example, detecting a change in capacitance generated by the detection target coming into contact with a surface of the operation reception unit 40. In a case in which the position acquisition unit 60 is the above-described electric field type position detection sensor, the position information of the detection target can be acquired even in a case in which, for example, the operator wears rubber gloves or the like, and a finger of the operator does not directly touch the operation reception unit 40.

Figure 3:
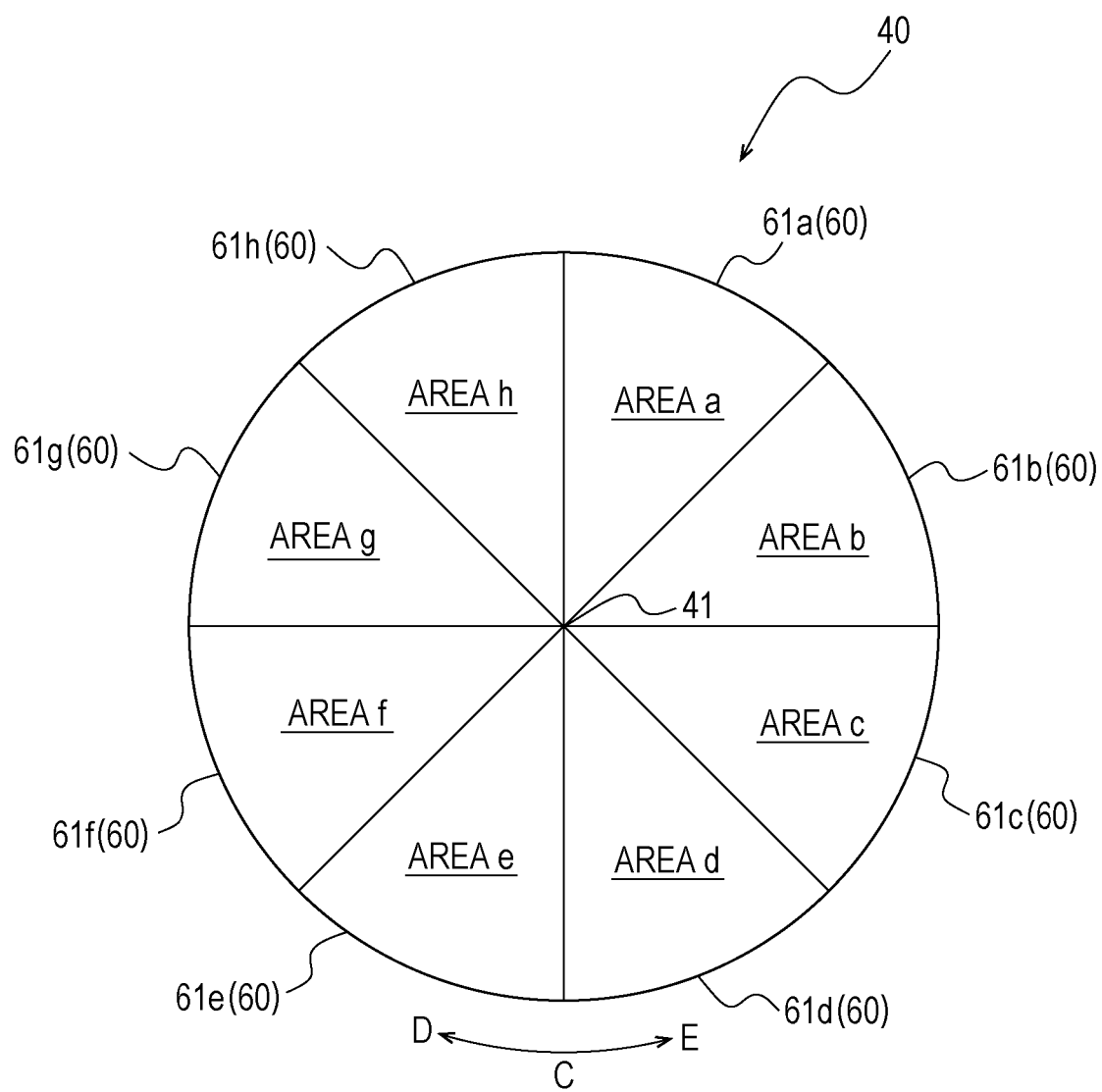
FIG. 3 illustrates a diagram of detection regions of a position acquisition unit included in the syringe pump illustrated in FIG. 1.

FIG. 3 is a diagram illustrating an arrangement of the detection regions as position information that can be acquired by the position acquisition unit 60. As illustrated in FIG. 3, the position acquisition unit 60 of the present embodiment has a plurality of detection regions arranged without a gap around a predetermined center point 41 on the operation reception unit 40, along circumferential directions C, which are, for example, eight fan-shaped detection regions 61a to 61h. Hereinafter, the eight detection regions 61a to 61h are also referred to as an area a to an area h, respectively.

The position acquisition unit 60 acquires, as position information of the detection target, a detection region closest to the detection target from among the plurality of detection regions 61a to 61h. Specifically, in a case in which the position acquisition unit 60 includes, for example, an electric field type position detection sensor, the position acquisition unit 60 acquires information indicating a position of the detection target in a three-dimensional space, and acquires, as position information of the detection target, a detection region closest to the position. In a case in which, for example, the position acquisition unit 60 includes a capacitance type position detection sensor, each of the plurality of detection regions can detect a contact of the detection target, and acquires, as position information of the detection target, a detection region where a contact is detected. The position acquisition unit 60 outputs information of the detection region as the acquired position information to the control unit 24. Hereinafter, position information of the detection target acquired by the position acquisition unit 60 will be described as "position information", and a detection region acquired, as position information of the detection target, by the position acquisition unit 60 will be described as an "acquired detection region".

As described above, the syringe pump 1 as the medical apparatus of the present embodiment includes the operation reception unit 40, the position acquisition unit 60 that can acquire position information of a detection target based on a position of the detection target on the operation reception unit 40, the detection target being in contact with or proximate to the operation reception unit 40, and the control unit 24 that identifies, on the basis of a change in the position information acquired by this position acquisition unit 60, operation input by the detection target. With this arrangement, the syringe pump 1 does not need to be provided with a rotary member that physically rotates as an input device, and therefore can limit reduction in operability even if a foreign substance such as liquid adheres. Moreover, because the syringe pump 1 does not need to be provided with a rotary member, the syringe pump 1 can be configured with a smaller gap. Therefore, cleanability can be improved.

[Processing by Syringe Pump]

Figure 4:
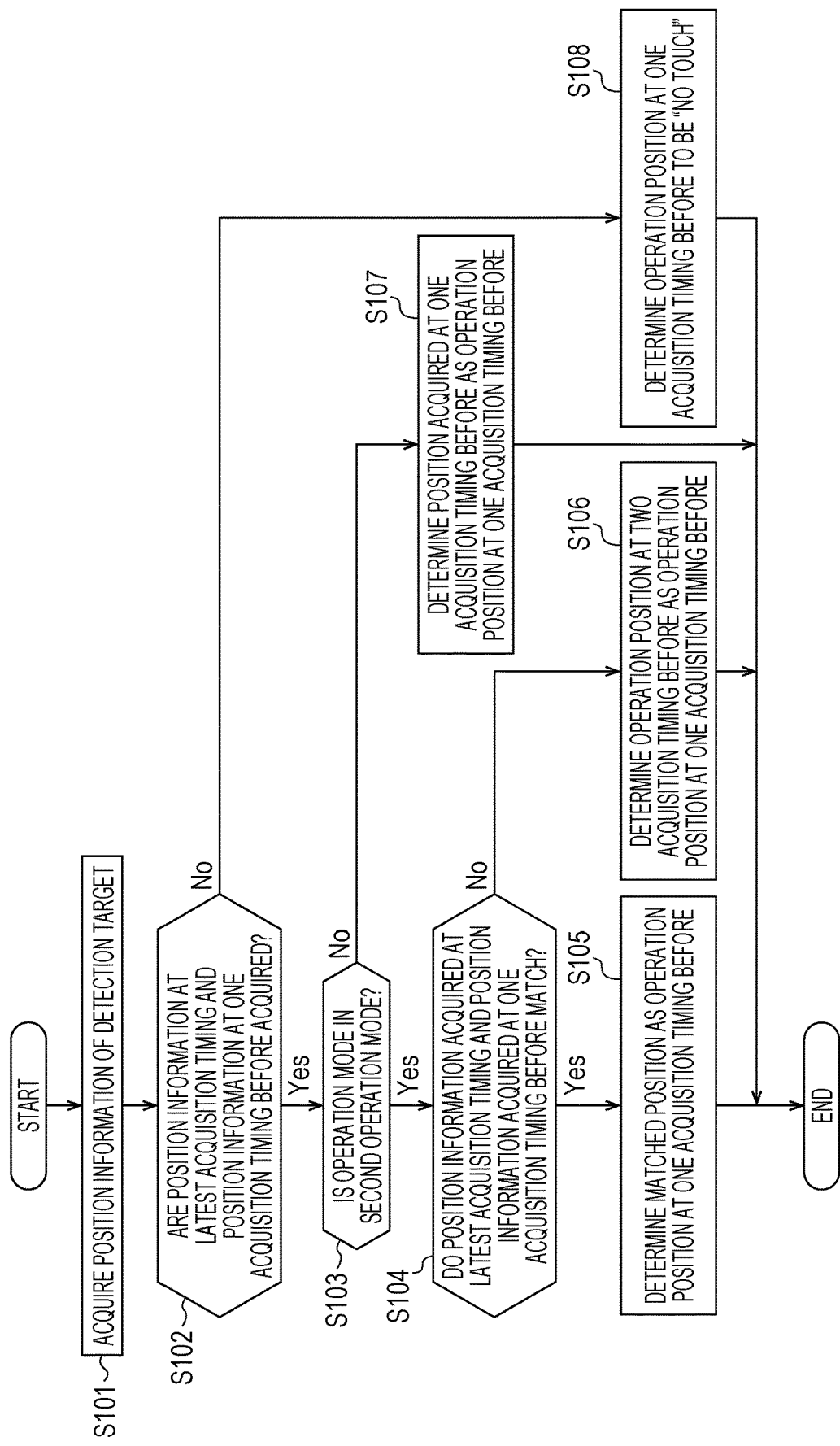
FIG. 4 is a flowchart that illustrates operation position determination processing performed by the syringe pump illustrated in FIG. 1.

FIG. 4 is a flowchart that illustrates an example of operation position determination processing performed by the syringe pump 1. The syringe pump 1 determines, with the control unit 24, the operation position of the detection target on the operation reception unit 40 on the basis of the position information acquired by the position acquisition unit 60. Here, the above-described position information is information about a detection region on the operation reception unit 40 of the detection target, the information being input from the operation reception unit 40 by the detection target actually being detected on the operation reception unit 40. Meanwhile, an operation position is a region on the operation reception unit 40, the operation position being determined on the basis of the above-described position information, and recognized as being input from the operation reception unit 40, instead of the above-described position information. The control unit 24 performs various kinds of control by regarding not the above-described position information, but the above-described operation position as the information input from the operation reception unit 40. Details of processing performed by the control unit 24 will be described below.

Here, the syringe pump 1 does not recognize, as the above-described operation position, the detection region on the operation reception unit 40 where the detection target has been actually detected, that is, the position information of the above-described detection target. With this arrangement, false operation may be avoided. For example, it is assumed that the operator is operating the operation reception unit 40 with a finger. At this time, for example, the operator performs operation while bringing a fingertip into contact with the operation reception unit 40. When the operator finishes the operation with respect to the operation reception unit 40 and tries to release the finger from the operation reception unit 40, in a case in which, for example, another portion other than the fingertip of the finger is in contact with the operation reception unit 40, the position acquisition unit 60 detects a position in which the another portion is in contact with the operation reception unit 40. In a case in which the syringe pump 1 performs some processing on the basis of such contact of another portion with the operation reception unit 40, the processing is unintended by the operator, and therefore the operation is false operation to the operator. Other than a case of releasing the finger, there may be a case in which the syringe pump 1 performs operation unintended by the operator due to contact of the finger with the operation reception unit 40, which is unintended by the operator. In such a case, the syringe pump 1 may avoid false operation by not recognizing the detection region where the detection target is actually detected as an operation position.

Therefore, in order to easily avoid false operation, the syringe pump 1 according to the present embodiment determines an operation position first, and then performs various pieces of processing, such as setting value increase/decrease processing for example, on the basis of the determined operation position. FIG. 4 illustrates an example of the operation position determination processing performed by the syringe pump 1.

In the operation position determination processing, the syringe pump 1 acquires position information of the detection target by using the position acquisition unit 60 (Step S101). The syringe pump 1 acquires position information at each acquisition time that occurs in a predetermined cycle, for example. Here, it is assumed that the position acquisition unit 60 acquires position information at a cycle of 10 milliseconds. In Step S101, the position information of the detection target at a latest acquisition time is acquired. The latest acquisition time is a last acquisition time by the position acquisition unit 60 at a certain time point (for example, present).

The position information acquired in Step S101 is sequentially stored in the storage unit 23 (refer to FIG. 2) of the circuit unit 20 (refer to FIG. 2) along with the acquired time, for example. In this way, the position information is accumulated in time series, for example.

The syringe pump 1 determines an operation position on the basis of the position information acquired in Step S101. In the present embodiment, the syringe pump 1 determines the operation position at a last acquisition time before the latest acquisition time on the basis of the acquired position information. Here, with reference to Step S102 to Step S106 illustrated in FIG. 4, an example of a case will be described where the syringe pump 1 determines, on the basis of position information acquired at a latest acquisition time, an operation position at a last acquisition time before the latest acquisition time, that is, at an acquisition time 10 milliseconds ago. In other words, this means that an operation position at the last acquisition time before the latest acquisition time is in an undetermined state, in which the operation position is not determined until position information is acquired at the latest acquisition time, which is one time after the last acquisition time before the latest acquisition time.

After acquiring the position of the detection information in Step S101, the syringe pump 1 judges whether or not the position information at the latest acquisition time and the position information at the last acquisition time before the latest acquisition time are acquired (Step S102). In a case in which the detection target is detected in, for example, any one area of the area a to area h in the operation reception unit 40 illustrated in FIG. 3 at the latest acquisition time and the last acquisition time before the latest acquisition time, the syringe pump 1 judges that position information has been acquired (Yes in Step S102). Meanwhile, in a case in which the detection target is not detected in, for example, any one area of the area a to area h in the operation reception unit 40 illustrated in FIG. 3 at at least one of the latest acquisition time or the last acquisition time before the latest acquisition time, the syringe pump 1 judges that position information is not acquired (No in Step S102). That is, in a case in which the syringe pump 1 judges that position information is not acquired, the operation reception unit 40 is not operated by the operator.

In a case in which the syringe pump 1 judges that the position information at the latest acquisition time and the position information at the last acquisition time before the latest acquisition time are acquired (Yes in Step S102), the syringe pump 1 judges whether or not the operation mode of the syringe pump 1 is in a predetermined operation mode (Step S103).

Here, an operation mode of the syringe pump 1 will be described. For example, the syringe pump 1 has a plurality of operation modes and operates in any one operation mode among the plurality of operation modes. In the present embodiment, as an example, the syringe pump 1 will be described as having two operation modes, which are a first operation mode and a second operation mode. The syringe pump 1 performs reception processing of input operation in either one operation mode of the first operation mode or the second operation mode according to input operation to the operation reception unit 40 by the finger of the operator, which is as the detection target.

The first operation mode is a mode that detects high-speed input by the finger of the operator, which is as the detection target. For example, in a case in which the operator is moving the finger in a state of being in contact with the operation reception unit 40 at a speed exceeding a predetermined threshold, that is, at a high speed, the syringe pump 1 operates in the first operation mode. The first operation mode is performed in a case in which, for example, the operator significantly changes a setting of a parameter, or the like, that is set in the syringe pump 1.

The second operation mode is a mode that detects low-speed input by the finger of the operator, which is as the detection target. For example, in a case in which the operator is moving the finger in a state of being in contact with the operation reception unit 40 at a speed of a predetermined threshold or lower, that is, at a low speed, the syringe pump 1 operates in the second operation mode. The second operation mode is performed in a case in which, for example, the operator tries to adjust a setting of a parameter, or the like, that is set in the syringe pump 1.

The syringe pump 1 stores, in the storage unit 23 for example, a criterion for judging whether input by a finger of the operator, which is as the detection target, is performed at a high speed or low speed. For example, in the example of the operation reception unit 40 described with reference to FIG. 3, the syringe pump 1 may judge that the input by the operator is performed at a high speed in a case in which the operator moves the finger by the predetermined number of areas or more within a predetermined time. On the contrary, in the example of the operation reception unit 40 described with reference to FIG. 3, the syringe pump 1 may judge that the input by the operator is performed at a low speed in a case in which the operator moves the finger by less than the predetermined number of areas within the predetermined time.

For example, the syringe pump 1 may perform processing in the first operation mode in a case in which movement across five or more areas within 50 milliseconds is detected. Furthermore, the syringe pump 1 may perform mode change processing from the second operation mode to the first operation mode in a case in which movement across five or more areas within 50 milliseconds is detected most recently. On the contrary, the syringe pump 1 may perform processing in the second operation mode in a case in which, for example, movement across less than five areas within 50 milliseconds is detected. Furthermore, the syringe pump 1 may perform mode change processing from the second operation mode to the first operation mode in a case in which, for example, movement across less than five areas within 50 milliseconds is detected most recently. It should be noted that a threshold that the syringe pump 1 uses for judging an operation mode may be determined as appropriate according to, for example, a size or shape of the operation reception unit 40, content of processing performed by the syringe pump 1, or the like.

In Step S103, the syringe pump 1 judges whether or not the operation mode is in the second operation mode, for example. As described above, the second operation mode is a mode performed in a case in which the operator tries to adjust a setting. At this time, for example, in a case in which the operator touches an unintended area while operating with an intention to release the finger from the operation reception unit 40, false operation occurs in which a setting for the syringe pump 1 changes. However, such false operation may be avoided by the operation position determination processing that will be specifically described below. For this reason, it is possible to reduce time and effort required to perform setting again due to the operation unintended by the operator and reduce stress on the operator.

In a case in which the syringe pump 1 judges that the operation mode is in the second operation mode (Yes in Step S103), the syringe pump 1 judges whether or not the position information acquired at the latest acquisition time and the position information acquired at the last acquisition time before the latest acquisition time match (Step S104).

FIG. 5 illustrates a diagram for describing an example of a method for determining an operation position by the syringe pump 1 in a case in which the operation mode is in the second operation mode at the latest acquisition time. FIG. 5 illustrates position information acquired by the position acquisition unit 60 and operation positions determined by the control unit 24. Names of each of the areas illustrated in FIG. 5 correspond to names of the areas (that is, the detection regions 61a to 61h) illustrated in FIG. 3, for example. Furthermore, the position information and operation positions illustrated in FIG. 5 are position information and operation positions at the latest acquisition time, the last acquisition time before the latest acquisition time, and the second to last acquisition time before the latest acquisition time.

The example illustrated in FIG. 5 indicates that the area h has been acquired as the position information at the second to last acquisition time before the latest acquisition time, the area a has been acquired as the position information at the last acquisition time before the latest acquisition time, which is 10 milliseconds after the second to last acquisition time before the latest acquisition time, and the area a has been acquired as the position information at a current acquisition time, which is further 10 milliseconds after the last acquisition time before the latest acquisition time. That is, in the example illustrated in FIG. 5, the position information at the latest acquisition time and the position information at the last acquisition time before the latest acquisition time match as "area a".

As illustrated in the example in FIG. 5, in a case in which the syringe pump 1 judges that the position information acquired at the latest acquisition time and the position information acquired at the last acquisition time before the latest acquisition time match (Yes in Step S104), the syringe pump 1 determines the matched position as the operation position at the last acquisition time before the latest acquisition time (Step S105). That is, in the example illustrated in FIG. 5, the syringe pump 1 determines the operation position at the last acquisition time before the latest acquisition time to be "area a". In this way, in a case in which the same position is acquired at two consecutive acquisition times, it is presumed that the operator is trying to operate so that the finger comes into contact with the position. Therefore, in a case in which the same position is acquired at two consecutive acquisition times, processing reflecting an intention of the operator can be performed by determining the position at a first acquisition time of the two consecutive acquisition times as the operation position, and then performing subsequent processing on the basis of the determined operation position.

FIG. 6 illustrates a diagram for describing an example of a method for determining an operation position by the syringe pump 1 in a case in which the operation mode is in the second operation mode at the latest acquisition time. As similar to FIG. 5, FIG. 6 also illustrates position information acquired by the position acquisition unit 60 and operation positions determined by the control unit 24.

The example illustrated in FIG. 6 indicates that the area h has been acquired as the position information at the second to last acquisition time before the latest acquisition time, the area a has been acquired as the position information at the last acquisition time before the latest acquisition time, which is 10 milliseconds after the second to last acquisition time before the latest acquisition time, and the area b has been acquired as the position information at a current acquisition time, which is further 10 milliseconds after the last acquisition time before. That is, in the example illustrated in FIG. 6, the position information at the latest acquisition time and the last acquisition time before the latest acquisition time are different in "area b" and "area a".

As illustrated in the example in FIG. 6, in a case in which the syringe pump 1 judges that the position information acquired at the latest acquisition time and the position information acquired at the last acquisition time before the latest acquisition time do not match (No in Step S104), the syringe pump 1 determines the operation position at the second to last acquisition time before the latest acquisition time as the operation position at the last acquisition time before the latest acquisition time (Step S106). That is, in the example illustrated in FIG. 6, the syringe pump 1 determines the operation position at the last acquisition time before the latest acquisition time to be "area g", which is the operation position of the second to last acquisition time before the latest acquisition time. For example, in a case in which the operator is trying to adjust a parameter, or the like, for the syringe pump 1 in input operation with respect to the operation reception unit 40, the operator may slowly move the finger as the detection target. At this time, for example, a contact state of the finger with respect to the operation reception unit 40 may become unstable, by which a contact position of the finger on the operation reception unit 40 may be deviated, and the finger may come into contact with an area unintended by the operator. However, as in Step S106, in a case in which different positions are acquired at the latest acquisition time and the last acquisition time before the latest acquisition time, processing reflecting an intention of the operator is easier to be performed by not treating positions acquired at the latest acquisition time and at the last acquisition time before the latest acquisition time as the operation position, but treating the operation position at the second to last acquisition time before the latest acquisition time as the operation position at the last acquisition time before the latest acquisition time, even if the finger is in contact with the area unintended by the operator, due to the unstable contact state of the finger.

With reference to Step S103 in FIG. 4 again, in a case in which the syringe pump 1 judges that the operation mode is not in the second operation mode (No in Step S103), that is, in a case in which the syringe pump 1 judges that the operation mode is in the first operation mode, the syringe pump 1 determines a position indicated by the position information acquired by the position acquisition unit 60 at the last acquisition time before the latest acquisition time as the operation position at the last acquisition time before the latest acquisition time (Step S107).

FIG. 7 illustrates a diagram for describing an example of a method for determining an operation position by the syringe pump 1 in a case in which the operation mode is in the first operation mode at the latest acquisition time. As similar to FIG. 5, FIG. 7 also illustrates position information acquired by the position acquisition unit 60 and operation positions determined by the control unit 24.

The example illustrated in FIG. 7 indicates that the area h has been acquired as the position information at the second to last acquisition time before the latest acquisition time, the area a has been acquired as the position information at the last acquisition time before the latest acquisition time, which is 10 milliseconds after the second to last acquisition time before the latest acquisition time, and the area b has been acquired as the position information at a current acquisition time, which is further 10 milliseconds after the last acquisition time before the latest acquisition time.

As illustrated in the example in FIG. 7, in a case in which the syringe pump 1 judges that the operation mode is in the first operation mode that detects high-speed input by the operator (No in Step S103), the syringe pump 1 determines a position indicated by the position information acquired by the position acquisition unit 60 at the last acquisition time before the latest acquisition time as the operation position at the last acquisition time before the latest acquisition time (Step S107). That is, in the example illustrated in FIG. 7, the syringe pump 1 determines the operation position at the last acquisition time before the latest acquisition time to be "area a", which is the position acquired at the last acquisition time before the latest acquisition time. For example, in a case in which the operator is performing high-speed input in input operation with respect to the operation reception unit 40, an operation position corresponding to input operation to move at a high speed, which is intended by the operator, can be determined by performing the processing like this, and therefore, processing corresponding to the input operation can be performed.

With reference to Step S102 in FIG. 4 again, in a case in which the syringe pump 1 judges that at least one of the position information at the latest acquisition time or the position information at the last acquisition time before the latest acquisition time is not acquired (No in Step S102), the syringe pump 1 determines the operation position at the last acquisition time before the latest acquisition time to be "no touch" (Step S108). Here, "no touch" indicates that no input has been made from the operation reception unit 40. That is, in a case of "no touch", the position information has not been acquired (detected).

FIG. 8 illustrates a diagram for describing an example of a method for determining an operation position by the syringe pump 1. As similar to FIG. 5, FIG. 8 also illustrates position information acquired by the position acquisition unit 60 and operation positions determined by the control unit 24. In FIG. 8, the operation mode at the latest acquisition time may be either the first operation mode or the second operation mode.

The example illustrated in FIG. 8 indicates that the area h has been acquired as the position information at the second to last acquisition time before the latest acquisition time, the area a has been acquired as the position information at the last acquisition time before the latest acquisition time, which is 10 milliseconds after the second to last acquisition time before the latest acquisition time, and "no touch" has been acquired as the position information at a current acquisition time, which is further 10 milliseconds after the last acquisition time before the latest acquisition time. As illustrated in FIG. 8, in a case in which the position acquisition unit 60 does not detect the detection target at the latest acquisition time, the syringe pump 1 determines the operation position at the last acquisition time before the latest acquisition time to be "no touch", that is, the detection target is not in an operation position on the operation reception unit 40. That is, although the position acquisition unit 60 actually detects the detection target in the area a as the position information at the last acquisition time before the latest acquisition time, the syringe pump 1 performs processing assuming that the detection target has not been detected at the last acquisition time before the latest acquisition time. With this arrangement, even if the position information acquired by the position acquisition unit 60 at the last acquisition time before the latest acquisition time reflects input operation unintended by a user, the syringe pump 1 does not treat the position information acquired at the last acquisition time before the latest acquisition time as an operation position, and therefore, occurrence of false operation can be avoided.

Figure 9:
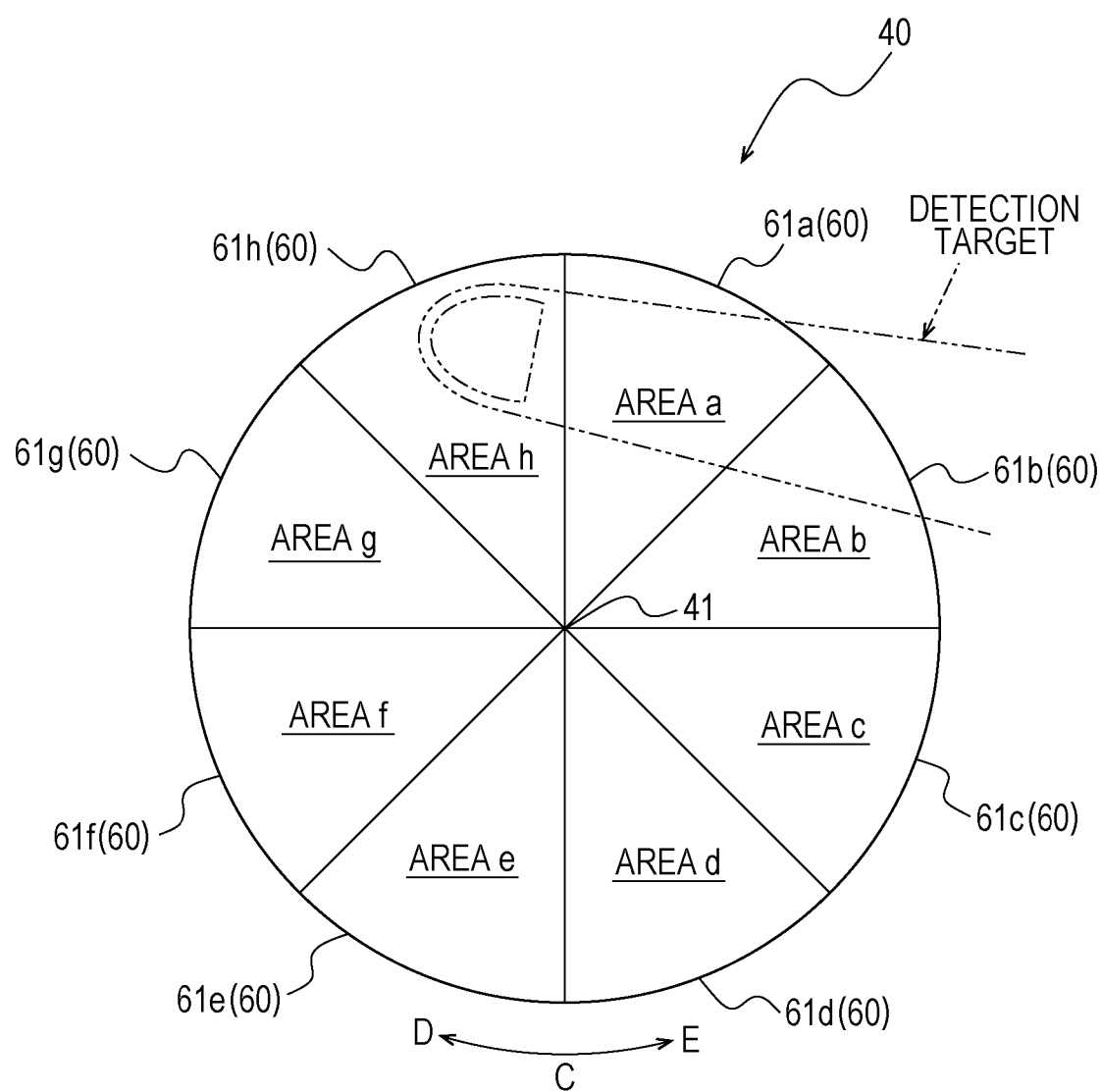
FIG. 9 illustrates a schematic diagram of an example of a state in which a finger as a detection target is released from an operation reception unit.

FIG. 9 illustrates a schematic diagram of an example of a state in which a finger as the detection target is released from the operation reception unit 40. For example, it is assumed that the operator is trying to release the finger in a state of being in contact with the area h from the operation reception unit 40, as illustrated in FIG. 9. At this time, for example, a portion other than the fingertip, such as a first joint of the finger, may come into contact with the area a. In a case in which a portion other than the fingertip is in contact with the area a after the operator releases the fingertip from the area h, the syringe pump 1 may determine that operation from the area h to the area a has been input. In such a case, false operation may occur. However, as described with reference to FIG. 7, in a case in which the position acquisition unit 60 does not detect the detection target at the latest acquisition time, the syringe pump 1 determines the operation position at the last acquisition time before the latest acquisition time to be "no touch", by which occurrence of false operation can be avoided.

It should be noted that, for example, in a case in which the operator is trying to release the finger as the detection target from the operation reception unit 40 after bringing the finger into contact with the area a, it is quite unlikely that the finger of the operator has moved from the area h to the area a after further 10 milliseconds, and is off the operation reception unit 40 after 10 milliseconds. In a case in which the operator is trying to release the finger from the operation reception unit 40 after bringing the finger into contact with the area a, the operation is considered usually that the finger is in contact with the area a for at least a few dozen milliseconds, and then released from the operation reception unit 40. In this case, the position acquisition unit 60 continually detects the detection target in the area a at several acquisition times. That is, the position acquisition unit 60 acquires position information indicating the area a at a plurality of times. Therefore, in this case, the area a is determined as the operation position except for the last one acquisition time among the several acquisition times, and then the operation position is determined to be "no touch" at the last acquisition time before the acquisition time at which "no touch" has been detected. Therefore, with the syringe pump 1 according to the present embodiment, determination of an operation position that meets an intention of the operator is possible even in a case in which the operator is trying to release the finger as the detection target from the operation reception unit 40 after bringing the finger into contact with the area a.

It should be noted that, as understood from FIGS. 5 to 8, the operation position at the last acquisition time before the latest acquisition time is determined after the position information at the latest acquisition time is acquired. Therefore, the operation position at the latest acquisition time is not determined and remains undetermined at a time when the position information at the latest acquisition time is acquired. The operation position at the latest acquisition time is determined after the position information at a next acquisition time is acquired.

The syringe pump 1 can perform various pieces of processing on the basis of the operation position determined in the operation position determination processing illustrated in FIG. 4, for example. Here, the setting value increase/decrease processing will be described as an example of the processing performed by the syringe pump 1.

Figure 10:
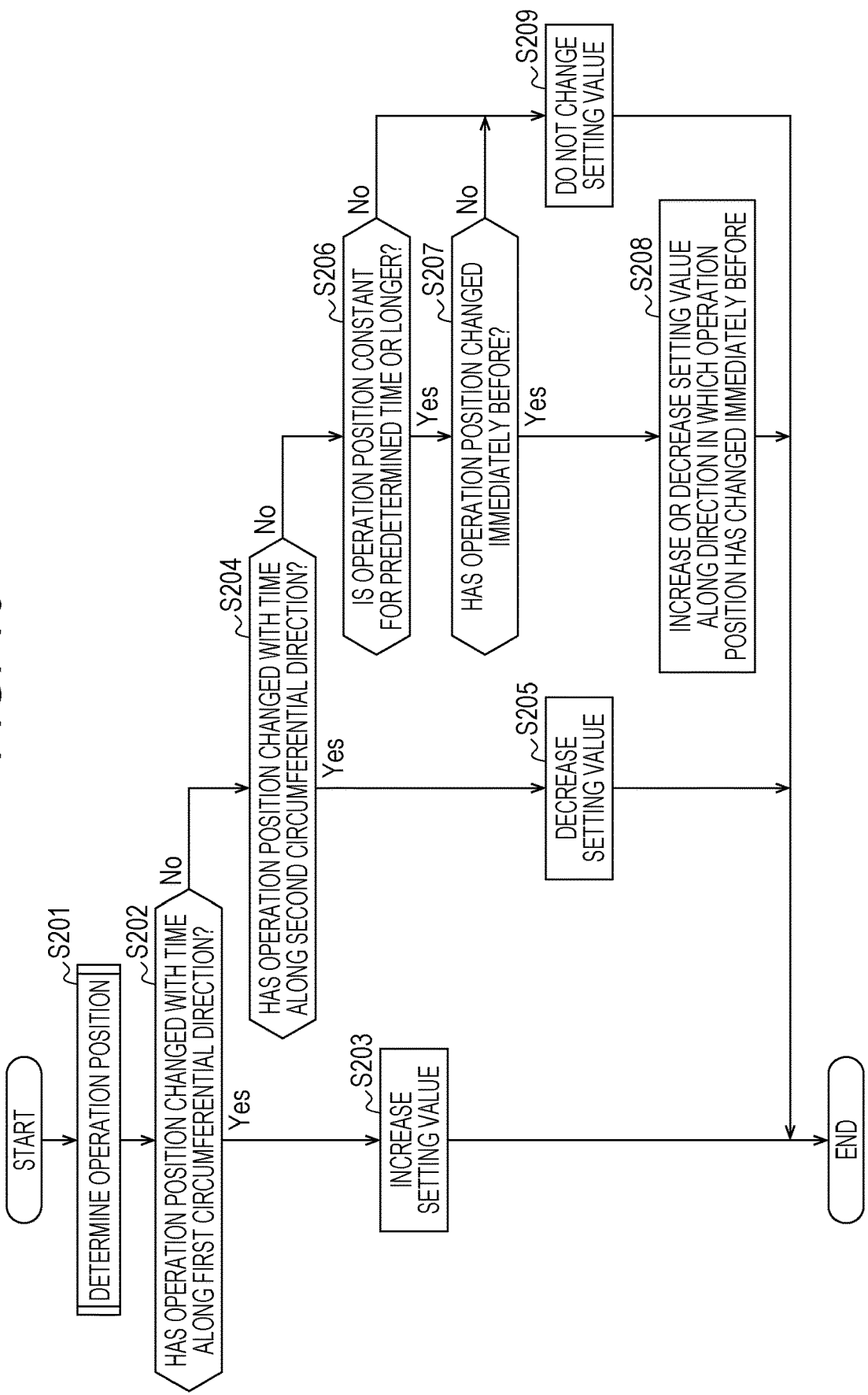
FIG. 10 is a flowchart that illustrates setting value increase/decrease processing performed by the syringe pump illustrated in FIG. 1.

FIG. 10 is a flowchart that illustrates setting value increase/decrease processing performed by the syringe pump 1. As illustrated in FIG. 10, the syringe pump 1 determines the operation position of the detection target on the operation reception unit 40 on the basis of the position information acquired by the position acquisition unit 60 (Step S201). Details of Step S201 are, for example, as in the operation position determination processing described with reference to FIG. 4. Here, it is assumed that an operation position other than "no touch" has been determined. That is, it is assumed that any one of the area a to the area h is determined as the operation position.

After that, the control unit 24 identifies the operation input by the detection target on the basis of a change in operation position with time. The control unit 24 increases or decreases a predetermined setting value on the basis of, for example, a change with time in an acquired detection region in the circumferential directions C (refer to FIG. 3). Specifically, the control unit 24 performs the processing in Steps S202 to S207 below.

The control unit 24 judges whether or not the operation position has changed with time along a first circumferential direction D (refer to FIG. 3), which is one of the circumferential directions C (Step S202). Specifically, the control unit 24 judges whether or not an acquired detection region has changed with time between two detection regions adjacent to each other, along the first circumferential direction D, that is, for example, whether or not the acquired detection region has changed with time from the area a to the area b.

In a case in which the control unit 24 judges that the operation position has changed with time along the first circumferential direction D (Yes in Step S202), the control unit 24 increases the predetermined setting value (Step S203). Meanwhile, in a case in which the control unit 24 judges that the operation position has not changed with time along the first circumferential direction D (No in Step S202), the processing proceeds to Step S204.

The control unit 24 judges whether or not the operation position has changed with time along another direction of the circumferential directions C, that is, a second circumferential direction E (refer to FIG. 3), which is a direction opposite to the first circumferential direction D (Step S204). Specifically, the control unit 24 judges whether or not an acquired detection region has changed with time between two detection regions adjacent to each other, along the second circumferential direction E, that is, for example, whether or not the acquired detection region has changed with time from the area a to the area h.

In a case in which the control unit 24 judges that the operation position has changed with time along the second circumferential direction E (Yes in Step S204), the control unit 24 decreases the predetermined setting value (Step S205). Meanwhile, in a case in which the control unit 24 judges that the operation position has not changed with time along the second circumferential direction E (No in Step S204), the processing proceeds to Step S206.

The control unit 24 judges whether or not the operation position is constant for a predetermined time or longer (Step S206). The predetermined time used in the processing in Step S206 is previously stored in the storage unit 23 and is, for example, 1 second.

In a case in which the control unit 24 judges that the operation position has been constant for the predetermined time or longer (Yes in Step S206), the control unit 24 judges whether or not the operation position has changed immediately before (Step S207). In other words, in the processing in Step S207, the control unit 24 judges whether or not the operation position up to immediately before the first operation position used as a basis of the judgement in the processing in Step S206 has changed. At this time, for example, in a case in which there has been a period in which the position information of the detection target cannot be acquired by the position acquisition unit 60 due to the detection target once leaving the operation reception unit 40, continuity from the change in the previous operation position is reset. That is, in a case in which the operation position is once determined to be "no touch", only the position information of the detection target continually acquired by the position acquisition unit 60 again becomes a target of the judgement in the processing in Step S207.

In a case in which the control unit 24 judges that the operation position has changed immediately before (Yes in Step S207), the control unit 24 increases or decreases the predetermined setting value along either the first circumferential direction D or the second circumferential direction E, whichever the direction in which the operation position has changed with time immediately before (Step S208). Specifically, the control unit 24 increases the predetermined setting value in a case in which the direction in which the operation position has changed with time immediately before is the first circumferential direction D. Meanwhile, the control unit 24 decreases the predetermined setting value in a case in which the direction in which the operation position has changed with time immediately before is the second circumferential direction E. After that, the control unit 24 continues to increase or decrease the predetermined setting value during a period in which the operation position is constant.

In a case in which the control unit 24 judges that the operation position has not been constant for the predetermined time or longer (No in Step S206), or judges that the operation position has not changed immediately before (No in Step S207), the control unit 24 does not change the predetermined setting value (Step S209).

As described above, the syringe pump 1 increases or decreases the predetermined setting value along a direction in which an operation position has changed with time immediately before in a case in which the operation position has been constant for the predetermined time or longer, and the operation position has changed immediately before, and therefore, the operator can continue to increase or decrease the predetermined setting value along the direction in which the detection target has been moved immediately before without continuing to move the detection target.

In the processing in Step S208, the control unit 24 may increase or decrease the predetermined setting value by a constant amount of change per unit time. With this arrangement, the operator can estimate remaining time until the predetermined setting value reaches a targeted value by checking, on the display unit 32, the predetermined setting value that changes at a constant speed, and therefore, can easily set the predetermined setting value to a targeted value.

In the processing in Step S208, the control unit 24 may increase or decrease the predetermined setting value by an amount of change per unit time corresponding to the amount of change per unit time in the position information that has changed immediately before. In other words, the control unit 24 may determine the amount of change in the predetermined setting value per unit time according to the amount of change per unit time in the position information that has changed immediately before. Specifically, the control unit 24 may increase the amount of change per unit time in the predetermined setting value as the amount of change per unit time in the position information that has changed immediately before is larger. In this way, the syringe pump 1 determines change speed of the predetermined setting value according to change speed of the position information that has changed immediately before, and therefore, can change the predetermined setting value at a speed corresponding to last operation by the operator.

Although in the above-described embodiment, the cycle in which the acquisition time occurs is 10 milliseconds, the cycle in which the acquisition time occurs is not limited to 10 milliseconds. The cycle in which the acquisition time occurs may be determined as appropriate according to, for example, a size or shape of the operation reception unit 40, content of processing performed by the syringe pump 1, or the like. The cycle in which the acquisition time occurs is preferably, for example, 5 milliseconds to 100 milliseconds, and more preferably 5 milliseconds to 50 milliseconds. By setting the cycle in which the acquisition time occurs to be equal to or less than an upper limit of the above range, in a case in which, for example, a position of the detection target is quickly changed, it is possible to reduce possibility of the control unit 24 erroneously recognizing that a direction in which the detection target actually has rotated is an opposite direction.

The present invention is not limited to the configurations specified in the above-described embodiment, and various modifications can be made without departing from the scope of the invention described in the claims. For example, the functions, or the like, included in each component, each step, or the like can be rearranged so as not to logically contradict, and a plurality of components, steps, or the like can be combined into one or divided.

Although the processing of increasing or decreasing a predetermined setting value on the basis of change in the operation position with time has been described as processing by the syringe pump 1 in the present embodiment, the processing is not limited to such processing. The processing by the syringe pump 1 may be any processing that identifies, on the basis of the change with time in the operation position, operation input by the detection target, such as switching a selection item, for example.

Although the medical apparatus is described as a syringe pump in the present embodiment, the medical apparatus is not limited to this. Examples of other medical apparatuses include a liquid delivery device, such as an infusion pump, a nutrition pump, and a blood pump, an ultrasonic image diagnostic device, an optical diagnostic imaging device, and the like.

The present disclosure relates to a medical apparatus and, in particular, to a medical apparatus that receives input operation by an operator.

REFERENCE NUMERAL LIST

1 Syringe pump (medical apparatus)
11 Placement unit
12 Slider
13 Pusher fixing unit
14 Clamp
15 Cylinder flange retainer
20 Circuit unit
21 Communication unit
22 Clocking unit
23 Storage unit
24 Control unit
31 Input button group
32 Display unit
36 Slider drive unit
40 Operation reception unit
41 Center point
46 Housing
50 Syringe
51 Cylinder
52 Hollow part 53 Cylinder flange
54 Outlet hole
55 Pusher
60 Position acquisition unit
61a to 61h Detection region
A Extending direction of cylinder of placed syringe
B Movable direction of clamp
C Circumferential direction
D First circumferential direction
E Second circumferential direction

The invention claimed is:

1. A medical apparatus comprising:
an operation reception unit;
a position acquisition unit configured to acquire position information of a detection target based on a position of the detection target that is in contact with or proximate to the operation reception unit at an acquisition time that occurs in a predetermined cycle; and
a control unit configured to:
determine an operation position of the detection target with respect to the operation reception unit at a last acquisition time before a latest acquisition time, on the basis of the position information acquired at the latest acquisition time and at the last acquisition time before the latest acquisition time, and
in a case in which the position information is not acquired at at least one of the latest acquisition time or at the last acquisition time before the latest acquisition time, determine that the detection target is not in the operation position on the operation reception unit at the last acquisition time before the latest acquisition time.

2. The medical apparatus according to claim 1, wherein, in a case in which the medical apparatus is in a predetermined operation mode, and position information acquired at the latest acquisition time and position information acquired at the last acquisition time before the latest acquisition time match, the control unit determines a position indicated by the matched position information as the operation position.

3. The medical apparatus according to claim 2, wherein the predetermined operation mode is a mode that detects low-speed input by the detection target.

4. The medical apparatus according to claim 3, wherein, in a case in which the detection target is moving in a state of being in contact with or proximate to the operation reception unit at a speed of a predetermined threshold or lower, the control unit operates in the mode that detects the low-speed input.

5. The medical apparatus according to claim 2, wherein, in a case in which an operation mode is not in the predetermined operation mode, the control unit determines a position indicated by position information acquired at the last acquisition time before the latest acquisition time as the operation position.

6. The medical apparatus according to claim 1, wherein, in a case in which the medical apparatus is in a predetermined operation mode, and position information acquired at the latest acquisition time and position information acquired at the last acquisition time before the latest acquisition time do not match, the control unit determines an operation position at a second to last acquisition time before the latest acquisition time as the operation position.

7. The medical apparatus according to claim 1, wherein the control unit is configured to increase or decrease a predetermined setting value on the basis of a change in the determined operation position in a circumferential direction around a predetermined center point on the operation reception unit.

8. The medical apparatus according to claim 1, wherein the position acquisition unit has a plurality of detection regions arranged along a circumferential direction around a predetermined center point on the operation reception unit, and is configured to acquire any one of the plurality of detection regions as the position information.

9. A syringe pump comprising:
an electric field type or capacitance type position detection sensor configured to acquire position information of a finger of an operator based on a position of the finger at an acquisition time that occurs in a predetermined cycle; and
a processor configured to:
determine an operation position of the finger at a last acquisition time before a latest acquisition time, on the basis of the position information acquired at the latest acquisition time and at the last acquisition time before the latest acquisition time, and
in a case in which the position information is not acquired at at least one of the latest acquisition time or at the last acquisition time before the latest acquisition time, determine that the detection target is not in the operation position on the operation reception unit at the last acquisition time before the latest acquisition time.

10. A medical apparatus comprising:
an operation reception unit;
a position acquisition unit configured to acquire position information of a detection target based on a position of the detection target that is in contact with or proximate to the operation reception unit at an acquisition time that occurs in a predetermined cycle; and
a control unit configured to:
determine an operation position of the detection target with respect to the operation reception unit at a last acquisition time before a latest acquisition time, on the basis of the position information acquired at the latest acquisition time and at the last acquisition time before the latest acquisition time, and
in a case in which the medical apparatus is in a predetermined operation mode, and position information acquired at the latest acquisition time and position information acquired at the last acquisition time before the latest acquisition time match, determine a position indicated by the matched position information as the operation position.

11. A medical apparatus comprising:
an operation reception unit;
a position acquisition unit configured to acquire position information of a detection target based on a position of the detection target that is in contact with or proximate to the operation reception unit at an acquisition time that occurs in a predetermined cycle; and
a control unit configured to:
determine an operation position of the detection target with respect to the operation reception unit at a last acquisition time before a latest acquisition time, on the basis of the position information acquired at the latest acquisition time and at the last acquisition time before the latest acquisition time, and
in a case in which the medical apparatus is in a predetermined operation mode, and position information acquired at the latest acquisition time and position information acquired at the last acquisition time before the latest acquisition time do not match, determine an operation position at a second to last acquisition time before the latest acquisition time as the operation position.

12. A syringe pump comprising:

an electric field type or capacitance type position detection sensor configured to acquire position information of a finger of an operator based on a position of the finger at an acquisition time that occurs in a predetermined cycle; and a processor configured to:
  determine an operation position of the finger at a last acquisition time before a latest acquisition time, on the basis of the position information acquired at the latest acquisition time and at the last acquisition time before the latest acquisition time, and
  in a case in which the medical apparatus is in a predetermined operation mode, and position information acquired at the latest acquisition time and position information acquired at the last acquisition time before the latest acquisition time match, determine a position indicated by the matched position information as the operation position.

13. A syringe pump comprising:

an electric field type or capacitance type position detection sensor configured to acquire position information of a finger of an operator based on a position of the finger at an acquisition time that occurs in a predetermined cycle; and a processor configured to:
  determine an operation position of the finger at a last acquisition time before a latest acquisition time, on the basis of the position information acquired at the latest acquisition time and at the last acquisition time before the latest acquisition time, and
  in a case in which the medical apparatus is in a predetermined operation mode, and position information acquired at the latest acquisition time and position information acquired at the last acquisition time before the latest acquisition time do not match, determine an operation position at a second to last acquisition time before the latest acquisition time as the operation position.

* * * * *